United States Patent [19]

Evanega et al.

[11] Patent Number: 4,743,536

[45] Date of Patent: May 10, 1988

[54] METHOD FOR ENZYME IMMUNO-DETERMINATIONS IN HETEROGENEOUS PHASE

[75] Inventors: George R. Evanega, Carmel, Ind.; Winfried Albert, Pähl, Fed. Rep. of Germany

[73] Assignee: Boehringer Mannheim GmbH, Mannheim, Fed. Rep. of Germany

[21] Appl. No.: 331,339

[22] Filed: Dec. 16, 1981

[30] Foreign Application Priority Data

Dec. 23, 1980 [DE] Fed. Rep. of Germany ....... 3048884

[51] Int. Cl.$^4$ ................. G01N 33/535; G01N 33/546
[52] U.S. Cl. ........................................ 435/7; 436/533; 436/534; 436/824; 436/500
[58] Field of Search .................. 435/7, 180, 178, 179; 436/500, 528, 529, 530, 533, 534, 824; 422/72

[56] References Cited

U.S. PATENT DOCUMENTS 3,654,090 4/1972 Schuurs et al. .......................... 435/7
4,299,916 11/1981 Litman et al. .......................... 435/7

OTHER PUBLICATIONS

Honig et al., Editor, The Van Nostrand Chemist's Dictionary, D. Van Nostrand Co., Inc., Princeton, N.J., p. 675 (1953).
Grant, Ed., Hackh's Chemical Dictionary, Fourth Edition, McGraw-Hill Book Company, N.Y., p. 649 (1969).

*Primary Examiner*—Esther M. Kepplinger
*Attorney, Agent, or Firm*—Felfe & Lynch

[57] ABSTRACT

Method for the determination of a component of the reaction between a specific binding protein and a substance bindable therewith which process comprises incubating a sample solution with a determined amount of binding component in insoluble form in the presence of a reagent containing a known amount of one of the binding components in enzyme-labeled form, separating the liquid phase from the solid phase by centrifuging and determining the activity of the enzyme remaining in the liquid phase in a centrifuge rotor during or after the action of increased gravitational force whereby the solid phase and the liquid phase are still in contact with one another.

The present invention provides a process for the determination of a component of the reaction between a specific binding protein and a substance bindable therewith by incubation of a sample solution with a previously ascertained amount of binding component in insoluble form in the presence of a reagent which contains a known amount of one of the binding components in enzyme labeled form, separation of the liquid phase from the solid phase by centrifuging and determination of the activity of the marker enzyme remaining in the liquid phase, wherein measurement of the enzyme activity is carried out in a centrifuge rotor during or after the action of increased gravitational force whereby the solid phase and the liquid phase are still in contact with one another.

8 Claims, 2 Drawing Sheets

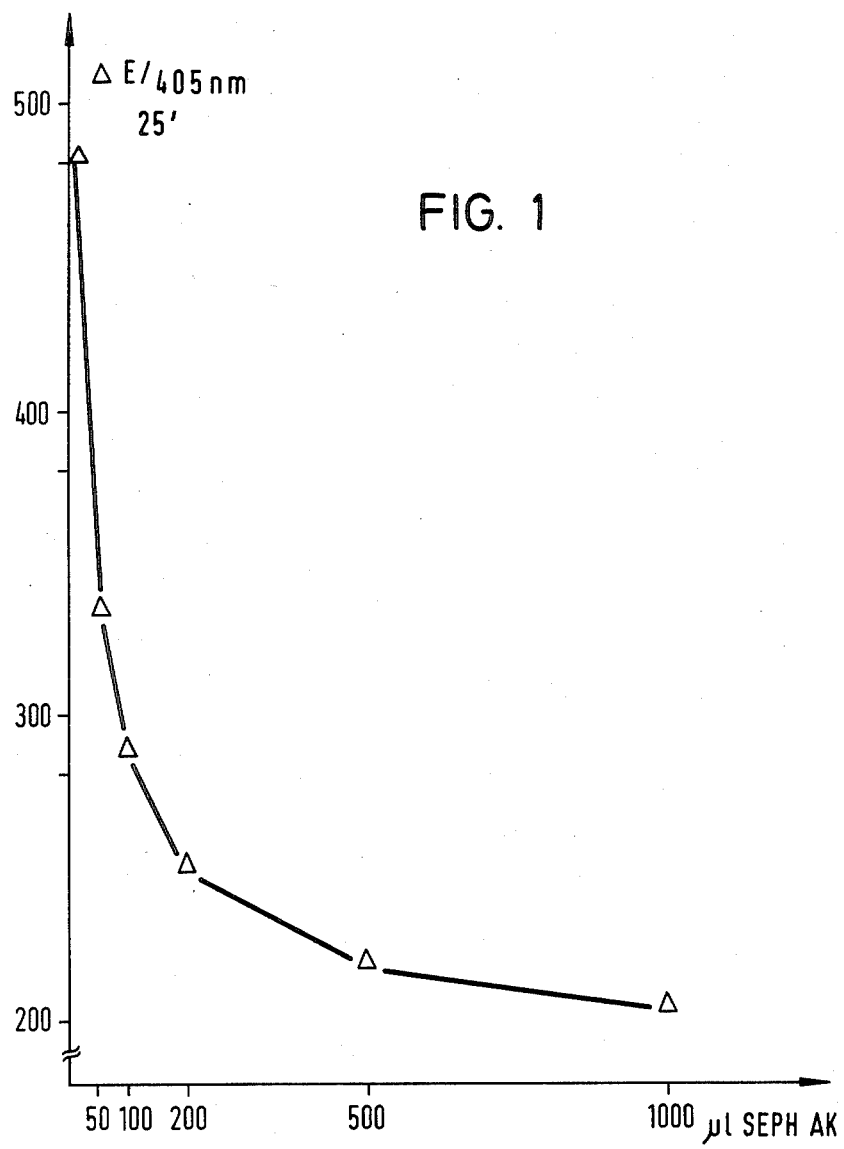

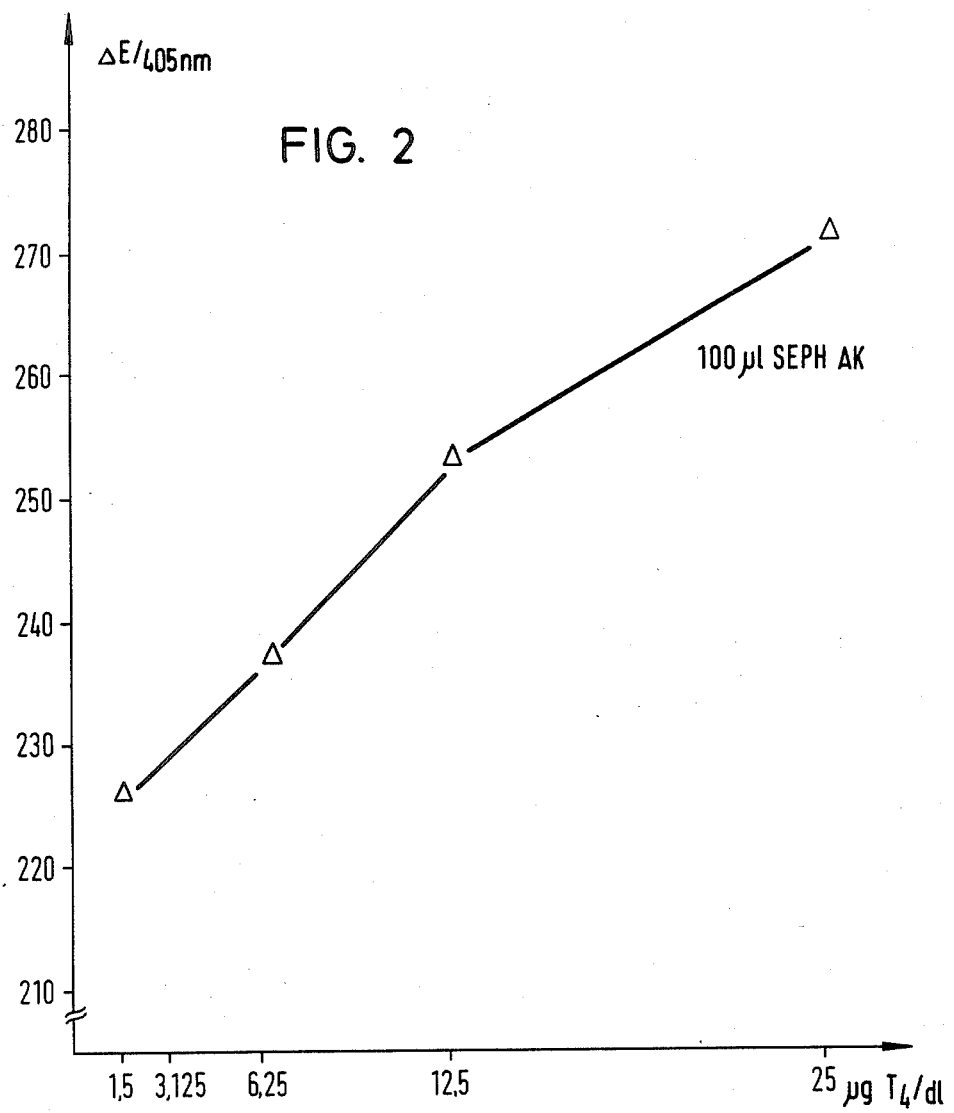

METHOD FOR ENZYME IMMUNO-DETERMINATIONS IN HETEROGENEOUS PHASE

This invention relates a method for the determination of a component of the reaction between a specific binding protein and a substance bindable therewith, utilizing the principle of the enzyme immuno process in the heterogeneous phase.

Because of the continuously increasing number of clinical-chemical analyses of serum components and similar biological materials, automation of such methods is of continuously increasing importance. Only by means of automation can the considerably increasing number of such determinations be accomplished and thereby the necessary expenditure of time per determination also reduced. Recently automatic analysers which depend upon the principle of centrifugal analysis have achieved great importance since they make possible a further increase of the analysis frequency without especial increase of the cost of the devices (G-i-T, Fachz. Lab., 21 (1977), 866–874).

For clinical diagnosis, in recent times the importance of processes for the determination of components of immune reactions has also increased. An important advance was thereby provided by the method of radio-immune analysis (RIA) since it also provided a substantial increase of the sensitivity of such determinations. A disadvantage of the RIA, namely, the necessity of having to handle radioactive substances, was overcome by the replacement of the radioactive labeling by an enzyme-label which gave rise to the so-called enzyme immuno assay (EIA). In the case of one embodiment of such a process, which is usually called the ELISA method, one component of the reaction between a specific binding protein and a substance bindable therewith is determined by incubating a sample solution with an unknown content of the substance to be determined with a previously determined amount of a binding component in insoluble form in the presence of a reagent which contains a known amount of one of the binding components in enzyme labeled form. After separation of the liquid phase from the solid phase, the activity of the marker-enzyme remaining in the liquid phase represents a measure for the unknown amount of the component of the immune reaction to be determined in the sample solution (cf. J. Clin. Chem. Clin., Biochem., 18, 197–208/1980). This heterogenous enzyme immuno test admittedly overcomes the necessity of having to work with radioactive substances but the separation step thereby necessary gives rise to difficulties in the case of automating and requires additional measures, such as are described, for example, in Federal Republic of Germany Patent Specification No. 2,736,527.

It is an object of the present invention to carry out such an enzyme immuno test process in such a manner that the automatability is improved and, in particular, can be performed in a centrifugal analyser.

Thus, according to the present invention, there is provided a process for the determination of a component of the reaction between a specific binding protein and a substance bindable therewith by incubation of a sample solution with a previously ascertained amount of binding component in insoluble form in the presence of a reagent which contains a known amount of one of the binding components in enzyme-labeled form, separation of the liquid phase from the solid phase by centrifuging and determination of the activity of the marker-enzyme remaining in the liquid phase, wherein measurement of the enzyme activity is carried out in a centrifugal rotor during or after the action of increased gravitational force whereby the solid phase and the liquid phase are still in contact with one another.

The present invention depends upon the very surprising fact that, under the influence of the gravitational force in a centrifugal rotor, the portion of the enzyme bound to the solid phase practically does not participate in the enzyme reaction so that, under the conditions according to the present invention, in the case of the measurement of the enzyme activity, only the enzyme present in the liquid phase is effective, whereas the bound enzyme in direct contact therewith but, as a result of the action of the increased gravitational force sedimented on the container wall, is not included in the determination. In the case of a centrifugal analyser, the components of a reaction are usually mixed under the influence of gravity and then passed onto a determination vessel, which is in the form of a cuvette in which the measurement is carried out during the running of the rotor. On the cuvette wall, upon which the gravitational force acts, in the case of the process of the present invention, the marker enzyme bound to the solid phase now collects and is, to that extent, admittedly removed from the light beam which passes through the cuvette for the measurement but still remains in contact with the reagent solution and can, therefore, also further participate in reactions in the reagent solution. This participation of enzymes bound in the solid phase in reactions in solution is technically used to a wide extent precisely in the case of carrier-bound enzymes. If action of the gravitational field had been expected in the case of such reactions, then, in any case, there was to have been expected an increased participation of the enzyme centrifuged on to the container wall since a migration of the reaction components under the influence of gravity, if at all, was only to be expected in the direction of its action, i.e. towards the enzyme present in the solid phase but not away from the solid phase.

The present invention renders superfluous the process steps hitherto regarded as being absolutely essential, i.e. separation of the solid phase and the liquid phase and washing of the solid phase (Dt. Ges.f.Klin.-Chem., Mitteilungen 1/79, 22–30) and the process becomes capable of being carried out on conventional centrifugal analysers. The serious hindrance in the case of carrying out the ELISA technique on automatic analysers is thus overcome.

The insoluble component of the enzyme reaction is, in the case of the process according to the present invention, preferably used in carrier-bound form. The carrier bonding can take place by methods known for immobilising biologically active material. Alternatively, the insoluble component can also be used in cross-linked form, for example, by a known reaction with a multifunctional cross-linking agent. Such cross-linking agents, such as glutardialdehyde and the like, are well known and do not need to be explained here in detail. Cross-linking and carrier fixing can also be combined, one component of the immune reaction thereby being fixed on to a carrier by cross-linking. Preferably, however, the insoluble component is used in particulate form, either by fixing on to a particulate carrier or by conversion into particulate form by carrier-free cross-linking.

The carrier for the insoluble component, when used, can be liquid or solid. According to an especially preferred embodiment of the present invention, the insoluble component of the immune reaction is bound to latex particles. An especial advantage of latex particles is their density which keeps them suspended in aqueous solution. Latex particles which are especially preferred for this purpose are described in Federal Republic of Germany Patent Application No. 30 48 883.6. These hydrophilic latex particles consist of a homo- or copolymer of monomers which are sparingly soluble in water and can be prepared by emulsion polymerisation in the presence of a water-soluble, radical-forming initiator but without the addition of an emulsifier, stabiliser or wetting agent. The preparation is carried out in an aqueous dispersion of the monomer or monomers by emulsion polymerisation in the absence of oxygen.

However, in the scope of the present invention, other carriers can also be used, such as are conventionally employed for fixing biologically active proteins, for example, insoluble carbohydrates, such as cellulose derivatives, cross-linked dextran, hydrophilic polymers and co-polymers, especially based upon acrylamide and the like.

The gravitational force necessary for carrying out the process according to the present invention corresponds to the values which normally occur in commercially available centrifugal automatic analysers.

All the other conditions which are to be maintained in carrying out the process correspond to the conditions known for the corresponding determination according to the ELISA technique. They are essentially determined by the pH and buffer dependability of the marker enzyme. These conditions are well known. Concentrations and incubation times can also correspond to the previously known values.

There are also no limitations with regard to the marker enzymes which can be used. All marker enzymes suitable for the ELISA technique can also be used in the case of the present invention.

The process according to the present invention can also be used with the various known modifications of the ELISA technique, for example the so-called competitive sandwich method, the sandwich antigen method, the sandwich antibody method and the immunoenzymometric method. These methods are schematically explained in the above-mentioned literature reference in J. Clin. Chem. Clin. Biochem. Examples of marker enzymes which can be used include peroxidase, glucose oxidase, galactosidase, alkaline phosphatase, glucoamylase, acetylcholine esterase and catalase.

Typical examples of antigens or haptens which can be determined with the process according to the present invention include thyroxine, digoxin, oestriol, $\alpha_1$-foetoprotein, insulin, thyrotropin, ferritin, carcinoembryonal antigen, $HB_2$-antigen and the like. The corresponding and any other desired antibodies can be determined in the same way.

The following Examples are given for the purpose of illustrating the present invention:

EXAMPLE 1

Reagents used:
(a) Sepharose-anti-$T_4$ antibody ($T_4$=tetraiodotyrosine=thyroxine)

1 g. Commercially available cyanogen bromide-activated, cross-linked agarose (Sepharose) was coupled, according to the manufacturer's instructions, with 10 ml. anti-$T_4$-immunoglobulin (anti-$T_4$-IgG from rabbits), the anti-$T_4$-IgG having been obtained from anti-$T_4$ antiserum by precipitation with 14% (w/v) ammonium sulphate solution.

(b) $T_4$-Glucose oxidase ($T_4$-GOD)

200 mg. (=1.07 μM) lyophilised glucose oxidase were dissolved in 20 ml. 0.1M phosphate buffer (pH 8.6) and mixed dropwise, while cooling and stirring, with 18.8 ml. dimethylformamide. To this solution were added 15 mg. (15.4 μM) BOC-$T_4$OSu (Su=succinimide), dissolved in 1.2 ml. dimethylformamide, within the course of 3 hours in 400 μl. portions. The reaction solution was kept for 20 hours at 4° C., while stirring and with the exclusion of light. A slight turbidity which appeared was centrifuged off. The supernatant solution was separated on a molecular sieve based upon cross-linked dextran (Sephadex G-25, fine) in 40 mM tris buffer (pH 7.5) and 150 mM sodium chloride. The first fraction (front) was collected (86 ml.). The solution obtained was dialysed twice against 12 liters of 40 mM phosphate buffer (pH 6.5). The resultant GOD-$T_4$-containing solution was, for the following experiment, diluted in the ratio of 1:10 with phosphate buffer (pH 6.5).

(c) Enzyme substrate solution.

20 mg. Peroxidase (POD), 4.6 g. 2,2'-azino-di(3-ethyl-benzthiazoline-6-sulphonate) and 50 g. glucose were brought to an end volume of 1 liter with 0.01M phosphate/citrate buffer (pH 5.6) containing 0.1% polyoxyethylenesorbitol monooleate (Tween 20).

(d) Carrying out of the experiment.

Various known amounts of the Sepharose-anti-$T_4$-IgG solution described under (a) (50/100/200/500/1000 μl.) were, in each case, mixed with 100 μl. of the $T_4$-GOD solution described under (b) and stirred for 15 minutes at ambient temperature. 35 μl. of this incubated mixture were introduced into the sample trough of a commercially available automatic centrifugal analyser (CentrifiChem 400). 60 μl. of the enzyme-substrate mixture described under (c) were introduced into the reagent region. Thereafter, centrifuging was carried out during which the extinction was measured at 405 nm. FIG. 1 of the accompanying drawings shows graphically the decrease of the extinction, measured after 25 minutes from the beginning of the centrifugation, plotted against the increase of the Sepharoseanti-$T_4$-IgG content.

EXAMPLE 2

100 μl. Sepharose-anti-$T_4$-IgG, 900 μl. 1M phosphate buffer (pH 7.0), 100 μl. $T_4$-GOD solution and 100 μl. of a $T_4$ standard in 0.1M phosphate buffer (pH 7.0) were stirred for 1 hour. 35 μl. of this incubation mixture were further treated on an automatic centrifugal analyser as described in Example 1 d). A calibration curve was obtained by using $T_4$ standard solutions of differing $T_4$ content. The determined values are shown in FIG. 2 of the accompanying drawings. Unknown $T_4$ concentrations can be determined by reference to this calibration curve. For this purpose, the above-described procedure was used but, instead of the $T_4$ standard solution, use is made of a corresponding amount of sample with unknown $T_4$ content.

EXAMPLE 3

Reagents used:
(a) Latex-anti-$T_4$- antibody $T_4$-antibodies from an anti-$T_4$ serum from sheep were covalently bound to homopolyglycidylmethacrylate latex particles (prepared according to Federal Republic of Germany Patent Application No.30 48 883.6) in the manner described therein.

(b) $T_4$-$\beta$-galactosidase ($T_4$-$\beta$-Gal)

$T_4$ was marked with $\beta$-Gal analogously to Example 1(b).

(c) $\beta$-Gal substrate solution 450 mg./l. p-nitrophenyl-$\beta$-galactoside (Sigma)
100 mM sodium chloride
10 mM magnesium chloride
10 mM tris buffer/HCl (pH 7.3)
0.4% (v/v) mercaptoethanol (d) Carrying out of the experiment 0.5 ml. of a diluted latex anti-$T_4$ suspension were mixed with 100 μl. amounts of $T_4$ serum standard solutions of different known $T_4$ content and 100 μl. of a $T_4$-$\beta$-Gal conjugate solution. The reaction mixture was left to stand for 30 minutes at ambient temperature. 35 μl. of each incubation mixture were introduced into the sample trough of a commercially available automatic centrifugal analyser (CentrifiChem 400). Into the reagent region of this centrifugal analyser were introduced 60 μl. of the substrate solution described under c). Thereafter, the mixture was centrifuged and the extinction was measured at a wavelength of 405 nm.

After a $T_4$ calibration curve has been produced in this way, determinations were subsequently carried out in the same way in which, instead of 100 μl. of $T_4$ standard serum, there were used 100 μl. amounts of samples of unknown $T_4$ content.

It will be understood that the specification and examples are illustrative but not limitative of the present invention and that other embodiments within the spirit and scope of the invention will suggest themselves to those skilled in the art.

We claim:

1. In a method for the determination of a component of the reaction between a specific binding protein and a substance bindable therewith by incubating a sample solution with a determined amount of binding component in insoluble form in the presence of a reagent containing a known amount of one of the binding components in enzyme-labeled form and determining the activity of the enzyme remaining in the liquid phase, the improvement comprising:

separating the liquid phase from the solid phase by centrifuging, and determining the activity of the enzyme remaining in the liquid phase in a centrifuge rotor during or after said separation of liquid or solid phase by centrifuging whereby the solid phase and the liquid phase are still in contact with one another.

2. Method as claimed in claim 1, wherein the insoluble component is used in carrier-bound form.

3. Method as claimed in claim 1, wherein the insoluble component is used in cross-linked form.

4. Method as claimed in claim 1, wherein the insoluble component is used in particulate form.

5. Method as claimed in claim 1, wherein the insoluble component is bound to latex particles.

6. Method as claimed in claim 1, wherein an antibody or anti-antibody is used as the insoluble component.

7. Method as claimed in claim 1, wherein an antigen, a hapten, an antibody or an anti-antibody is used as the enzyme labeled component.

8. Method as claimed in claim 1, wherein an antigen or a hapten is used as the insoluble component and an antibody is used as the enzyme labeled component.

* * * * *